US005461081A

United States Patent [19]
Ali et al.

[11] Patent Number: 5,461,081
[45] Date of Patent: Oct. 24, 1995

[54] TOPICAL OPHTHALMIC PHARMACEUTICAL VEHICLES

[75] Inventors: Yusuf Ali, Forth Worth, Tex.; Kenneth W. Reed, Lawrenceville, Ga.

[73] Assignee: Alcon Laboratories, Inc., Fort Worth, Tex.

[21] Appl. No.: 178,941

[22] Filed: Jan. 7, 1994

Related U.S. Application Data

[63] Continuation-in-part of Ser. No. 109,748, Aug. 20, 1993, abandoned, which is a continuation-in-part of Ser. No. 913,110, Jul. 14, 1992, abandoned, which is a continuation-in-part of Ser. No. 414,550, Sep. 28, 1989, abandoned.

[51] Int. Cl.$^6$ .................. A61K 47/00; A61K 31/715
[52] U.S. Cl. .................. 514/772.3; 514/54; 514/781; 514/782; 514/912
[58] Field of Search .................. 514/772.3, 781, 514/782, 54, 912

[56] References Cited

U.S. PATENT DOCUMENTS

| | | | |
|---|---|---|---|
| 4,136,173 | 1/1979 | Pramoda et al. | 424/177 |
| 4,615,697 | 10/1986 | Robinson | 604/890 |
| 4,616,012 | 10/1986 | Neustadt et al. | 514/222 |
| 4,638,059 | 1/1987 | Sutherland | 536/121 |
| 4,692,954 | 9/1987 | Mich et al. | 514/312 |
| 4,783,444 | 11/1988 | Watkins et al. | 514/19 |
| 4,795,436 | 1/1989 | Robinson | 424/422 |
| 4,861,760 | 8/1989 | Mazuel et al. | 514/54 |
| 4,911,920 | 3/1990 | Jani et al. | 424/78 |
| 4,983,392 | 1/1991 | Robinson | 424/427 |
| 5,188,826 | 2/1993 | Chandrasekaran et al. | 424/78.04 |
| 5,192,535 | 3/1993 | Davis et al. | 424/78.04 |
| 5,212,162 | 5/1993 | Missel et al. | 514/54 |

FOREIGN PATENT DOCUMENTS

| | | |
|---|---|---|
| 0495421A1 | 7/1992 | European Pat. Off. . |
| 2007091A | 8/1979 | United Kingdom . |
| WO89/06964 | 8/1989 | WIPO . |
| WO91/19481 | 12/1991 | WIPO . |

OTHER PUBLICATIONS

Saettone et al., "Vehicle effects on ophthalmic bioavailability: the influence of different polymers on the activity of pilocarpine in rabbit and man," *J. Pharm. Pharmacol.*, vol. 34 pp. 464–466 (1982).

B. F. Goodrich Carbopol® Resins–Product Information (1991).

*Primary Examiner*—Zohreh Fay
*Attorney, Agent, or Firm*—Patrick M. Ryan; Sally Yeager

[57] ABSTRACT

Universal ophthalmic pharmaceutical vehicles which increase in viscosity upon instillation in the eye are disclosed. Ophthalmic compositions of the universal vehicle and a pharmaceutically active drug are also disclosed. In one embodiment, the vehicle gels upon instillation in the eye. In another embodiment, suspension vehicles having superior physical stability are provided.

19 Claims, 1 Drawing Sheet

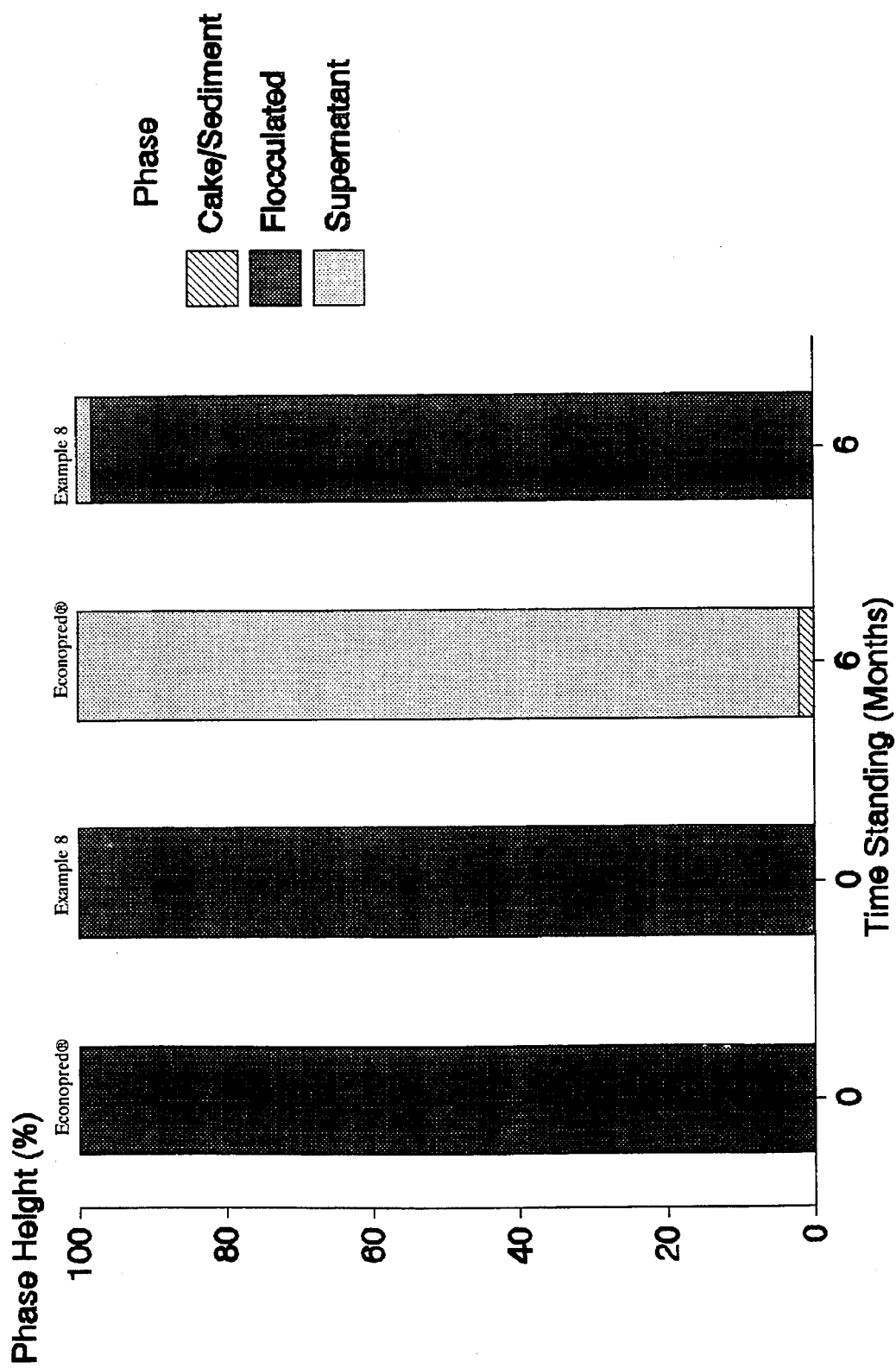

5,461,081

TOPICAL OPHTHALMIC PHARMACEUTICAL VEHICLES

This application is a continuation-in-part of U.S. Ser. No. 08/109,748, filed Aug. 20, 1993, now abandoned, which is a continuation-in-part of U.S. Ser. No. 07/913,110, filed Jul. 14, 1992, now abandoned, which is a continuation-in-part of U.S. Ser. No. 07/414,550, filed Sep. 28, 1989, now abandoned.

BACKGROUND OF THE INVENTION

This invention is directed to liquid ophthalmic pharmaceutical vehicles which become viscous on contacting the eye. This invention also relates to topical ophthalmic compositions comprising the vehicle and a pharmaceutically active drug.

It is known that the addition of viscous or visco-elastic polymers to an eye drop pharmaceutical composition will increase the viscosity of the composition. This is usually desirable on the premise that an increased vehicle viscosity enhances drug delivery and duration of action; see, for example, *J. Pharm. Pharmacol.*, Vol. 34, pp. 464–466 (Jan. 7, 1982). However, it is frequently advantageous to administer ophthalmic compositions as a drop, that is, an aqueous solution or suspension rather than a thick, viscous gel or ointment which can be messy and may tend to blur vision. In addition, non-droppable compositions can present problems with patient compliance, especially with the elderly.

Another problem, in the case of suspension compositions, is their poor physical stability. Many marketed ophthalmic suspension products currently use the polymers hydroxypropyl methylcellulose, hydroxyethyl cellulose, and polyvinyl alcohol to increase the suspension's viscosity and thus decrease the settling rate of the drug particles. These suspensions are not well flocculated and, with time, the insoluble drug particles will completely settle forming a dense layer which will not resuspend easily. This in turn may undesireably lead to variable drug dosages.

SUMMARY OF THE INVENTION

The present invention provides for ophthalmic vehicles and compositions which can be administered as a drop, but whose viscosity increases upon instillation into the eye so that the composition provides for relatively better drug delivery and duration of action, referred to herein as bioavailability, of drug over aqueous compositions whose viscosity does not increase upon instillation. In one embodiment the vehicle gels upon instillation. In another embodiment, the vehicle provides an improved suspension vehicle.

This invention relates to ophthalmic pharmaceutical vehicles and compositions comprising the vehicle and a pharmaceutically active drug in which the vehicle comprises a charged polymer and oppositely charged electrolytes or molecules, hereinafter referred to collectively as "electrolytes", which can be administered as a drop and upon instillation, increase in viscosity. The polymer can be negatively charged, such as a carboxyvinyl polymer, in which case the vehicle will include positively charged electrolytes, such as calcium. Conversely, the polymer can be positively charged and then negatively charged electrolytes are used in the vehicle.

The suspension vehicles of the present invention possess improved suspension characteristics. They exhibit superior physical stability and permit easy resuspension of insoluble drug particles, thus resulting in greater uniformity of drug dosing. In addition to an ophthalmic dosage form, the vehicles and compositions of the present invention also provide for oral, parenteral and topical suspension dosage forms.

The vehicles of this invention can be used in composition with pharmaceutically active drugs. The term "drug", as used herein, means any therapeutic agent that is desirable to deliver to the eye. There is no limitation on the type of drug which can be incorporated into the compositions disclosed herein. The drugs can be charged, uncharged, water soluble or insoluble.

BRIEF DESCRIPTION OF THE DRAWINGS

FIG. 1 compares the physical stability of two suspensions.

DETAILED DESCRIPTION OF PREFERRED EMBODIMENTS

The vehicles disclosed herein comprise a charged polymer and oppositely charged electrolytes. Without intending to be bound by any theory, it is understood that the vehicle's viscosity is increased due to the decrease in electrolyte concentration when the vehicle is administered to the eye. In the case of a gelling vehicle, the concentrations of the polymer and electrolytes in the vehicle are optimal when a small change in electrolyte concentration will result in a dramatic increase in vehicle viscosity. The small change in electrolyte concentration on instillation is caused by the electrolytes being taken up by the cells in the eye, by diffusing out of the polymer vehicle or being eliminated in tear fluid or by a combination of these mechanisms. Whatever the mechanism, the concentration of electrolytes in the vehicle is reduced and the vehicle viscosity increases.

As used herein, "gels" means the vehicle's viscosity increases sufficiently to transform the drop into a semi-solid or gelatinous state.

Polymers which can be used in the vehicle disclosed herein include any nontoxic charged water soluble polymer. These polymers can either be negatively or positively charged. Typically, negatively charged polymers will include, but are not limited to, carboxy vinyl polymers, such as Carbopol®, sodium carboxy methylcellulose, pectin, gelatin (Type B), sodium hyaluronate, acacia, calcium carboxy methylcellulose, sodium alginate and polystyrene sulfonic acid (PSSA). These polymers are used in the vehicles at concentrations from about 0.1 to about 10.0 weight percent (wt. %).

Electrolytes which are used in conjunction with the charged polymers will be either cations or anions depending on the charged polymer being used. If negatively charged polymers are being used in the vehicle the electrolytes which are used to provide for the changing viscosity upon instillation will be positively charged. These cations will typically be $Na^+$, $K^+$, $Mn^{++}$, $Ca^{++}$, $Mg^{++}$, $Fe^{++}$, $Fe^{+++}$, $Al^{+++}$, $Li^+$, $Zn^{++}$ and $Be^{++}$. In addition, positively charged organic ions can be used, for example, lysine∘HCl, arginine∘HCl and histadine∘HCl. These electrolytes will typically be present at a concentration of between 0.01 and 1.0 wt. %.

If a positively charged polymer is used, such as gelatin (Type A) or polyvinyl amine, the electrolyte used in conjunction therewith to provide for viscosity changes will be an anion. These anions will typically be $PO_4^{-3}$, $HPO_4^{-2}$, $H_2PO_4^-$, $I^-$, $Cl^-$, $F^-$, $SO_4^{-2}$, $HCO_3^-$ and negatively charged organic ions. Again, the polymer concentration will range from about 0.1–10.0 wt. % and the electrolytes will typically be present at a concentration of between about 0.01 wt. % to about 1.0 wt. %.

The concentrations of the polymers and corresponding electrolytes in the vehicles of the present invention are adjusted to provide for compositions in which the viscosity is such that the composition can be administered as a drop topically (typically, about 200 to about 2000 cps.). Upon instillation in the eye, the electrolyte concentration will change resulting in an increase in viscosity. The resulting compositions allow for the delivery of a drag in drop form, but provide for enhanced drug delivery due to the compositions' increased viscosity once in the eye. Depending on the specific combination of polymer and electrolyte concentration, in conjunction with any other ingredients, such as the drug, the small change in electrolyte concentration which occurs upon instillation in the eye may provide for a large increase in viscosity such that the vehicle gels. If the concentration level of polymer to electrolyte is too high, the vehicle will not be easily administrable as a drop. Conversely, it is too low, the vehicle will not undergo any significant viscosity increase upon instillation.

An impoved suspension vehicle is obtained when the polymer to electroylte concentration is low. Although such vehicles may not experience an increase in viscosity sufficient to transform the vehicle into a gel upon instillation, they do exhibit superior physical stability. The polymer acts to flocculate the insoluble particles by providing a stearic barrier and the electrolytes act to decrease the viscosity of the vehicle to about 200 cps or less, typically to about 75 cps to 150 cps, for easy dispensability from a plastic drop dispensing bottle. The insoluble particles may be resuspended easily for uniform dosing. Compositions containing a water-insoluble drug compound which possess such relatively low polymer and electrolyte concentration levels do exhibit superior physical stability, however. The polymer acts to flocculate the insoluble particles and the electrolytes act to decrease the viscosity of the vehicle. The insoluble particles may be resuspended easily for uniform dosing and can be dispensed from a plastic drop dispensing bottle.

Preferably, the polymers are negatively charged in both cases above, and more preferably, the polymers are the carboxy vinyl polymers available from B. F. Goodrich under the product name Carbopol®. Most preferred are the Carbopol® 934P polymers. The corresponding preferred electrolytes are therefore positively charged. Most preferred are the $Na^+$, $Ca^{++}$, and $Al^{+++}$ cations. Most preferred for gelling vehicles are $Ca^{++}$, $Mg^{++}$, $Zn^{++}$, and $Al^{+++}$. Most preferred for suspension vehicles are $Na^+$, $Zn^{++}$, and $Al^{+++}$.

Carbopol® is particularly preferred for the ophthalmic vehicles of the present invention because it has low ocular toxicity, it is an effective polyelectrolyte when neutralized in the pH range near seven, it is a long chain polymer which may adsorb onto the surface of suspended particles, thus providing stearic hindrance to the particles agglomerating, and the viscosity of formulations containing Carbopol® is easily optimized through the use of positively charged species. In this preferred case where the polymer is Carbopol®, the maximum concentration of polymer in the vehicles of the present invention will be approximately 3 wt. % or less.

The vehicles of this invention may be used as carriers for a wide variety of pharmaceutically active, water-insoluble drugs; these vehicles may therefore be called "universal" ophthalmic vehicles. Drugs which can be delivered in the vehicles of the present invention include, but are not limited to, steroids, growth factors, antioxidants, aldose reductase inhibitors, non steroidal antiinflammatories, immunomodulators, anti-allergics, antimicrobials, and beta-blockers. If the drug particles are charged, the concentrations of the polymer and electrolyte are adjusted so that the vehicle's viscosity allows for topical drop administration. The concentrations of the polymer and corresponding electrolyte are dependant upon the nature of the polymer itself, the nature of the drug/polymer charge interaction or lack thereof, the desired amount of drug retention time in the eye and, in the case of a suspension, whether the vehicle is optimized for physical stability or viscosity increase upon instillation.

In addition to the principal active ingredients, the vehicles and compositions of the present invention may further comprise various formulatory ingredients, such as antimicrobial preservatives and tonicity agents. For example, antimicrobial preservatives include: benzalkonium chloride, thimerosal, chlorobutanol, methylparaben, propylparaben, phenylethyl alcohol, EDTA, Hamposyl®, sorbic acid, Polyquad® and other agents equally well known to those skilled in the art. Such preservatives, if employed, will typically be used in an amount from about 0.0001 wt. % to 1.0 wt. %. Suitable agents which may be used to adjust tonicity or osmolality of the compositions include: mannitol, dextrose, glycerine and propylene glycol. If used, such agents will be employed in an amount of about 0.1 wt. % to 10.0 wt. %. However, preferable composition of the present invention will not include preservatives or tonicity agents which are known to adversely affect or irritate the eye, particularly the cornea.

The following Examples illustrate certain embodiments of the vehicles and compositions of this invention and are not intended to limit the scope of the present invention in any way.

EXAMPLES 1–4:

Universal ophthalmic gelling vehicles which are administrable as a drop, but which gel upon instillation in the eye. If charged drug particles are added to these vehicles, the electrolyte concentration may have to be adjusted so that the composition remains administrable as a drop but gels upon instillation.

EXAMPLE 1

| Ingredient | Weight Percent |
| --- | --- |
| Carbopol ® 934P | 0.30 |
| Calcium Chloride | 0.045 |
| Mannitol | 4.50 |
| NaOH | pH 7.2 ± 0.2 |
| Purified Water | q.s. 100% |

Preparation

The recommended compounding procedure for preparing "Universal" Ophthalmic Vehicle No. 1 is as follows:

1. Tare a labeled vessel, weight the Carbopol® into the vessel and begin agitation.

2. Add the remaining ingredients and stir until well dispersed.

3.

Add sufficient purified water to adjust the weight to 80% of total batch weight.

4. Adjust the pH to 7.2+0.2 using only sodium hydroxide. Use hydrochloric add only if absolutely necessary, and they in the smallest quantities need to obtain the target pH range.

5. QS to 100% of the final batch weight with purified water.
6. Steam sterilize the formulation.

The vehicles of Examples 2–6 were also prepared according to this compounding procedure.

EXAMPLE 2

"Universal" Ophthalmic Vehicle No. 2

| Ingredient | Weight Percent |
|---|---|
| Carbopol ® 934P | 0.40 |
| Calcium Chloride | 0.10 |
| Mannitol | 4.00 |
| NaOH | pH 7.2 ± 0.2 |
| Purified Water | q.s. 100% |

EXAMPLE 3

"Universal" Ophthalmic Vehicle No. 3

| Ingredient | Weight Percent |
|---|---|
| Carbopol ® 934P | 0.40 |
| Calcium Chloride | 0.05 |
| Lysine HCl | 0.225 |
| Mannitol | 4.00 |
| NaOH | pH 7.2 ± 0.2 |
| Purified Water | q.s. 100% |

EXAMPLE 4

"Universal" Ophthalmic Vehicle No. 4

| Ingredient | Weight Percent |
|---|---|
| Carbopol ® 934P | 1.00 |
| Calcium Chloride | 0.40 |
| Mannitol | 3.00 |
| KOH | pH 7.2 ± 0.2 |
| Purified Water | q.s. 100% |

EXAMPLES 5–6:

Universal ophthalmic pharmaceutical suspension vehicles which exhibit superior physical stability. If charged drug particles are added to these suspension vehicles, an appropriate adjustment may have to be made to the electrolyte concentration.

EXAMPLE 5

"Universal" Pharmaceutical Vehicle No. 1

| Ingredient | Weight Percent |
|---|---|
| Mannitol | 1.80 |
| Carbopol ® 934P | 0.45 |
| Polysorbate 80 | 0.05 |
| Sodium Chloride | 0.50 |
| Edetate Disodium | 0.01 |
| Benzalkonium Chloride | 0.01 + 5% excess |
| NaOH | pH 7.2 ± 0.2 |

-continued

| Ingredient | Weight Percent |
|---|---|
| Purified Water | q.s. 100% |

EXAMPLE 6

"Universal" Pharmaceutical Vehicle No. 2

| Ingredient | Weight Percent |
|---|---|
| Carbopol ® 934P | 0.70 |
| Polysorbate 80 | 0.05 |
| Sodium Chloride | 0.80 |
| Edetate Disodium | 0.01 |
| Benzalkonium Chloride | 0.01 + 5% excess |
| NaOH | pH 7.2 ± 0.2 |
| Purified water | q.s. 100% |

EXAMPLE 7

Preferred Ophthalmic Gelling Solution

| Ingredient | Weight Percent |
|---|---|
| Betaxolol HCl | .28 |
| Carbopol ® 934P | 1.00 |
| Calcium Chloride | .75 |
| Mannitol | 1.5 |
| Benzalkonium Chloride | 0.01 |
| EDTA | .05 |
| NaOH | pH 7.2 ± 0.2 |
| Purified Water | q.s. 100% |

EXAMPLE 8

Preferred Suspension Composition

| Ingredient | Weight Percent |
|---|---|
| Rimexolone | 1.0 |
| Mannitol | 1.80 |
| Carbopol ® 934P | 0.45 |
| Polysorbate 80 | 0.05 |
| Sodium Chloride | 0.50 |
| Edetate Disodium | 0.01 |
| Benzalkonium Chloride | 0.01 + 5% excess |
| NaOH | pH 7.2 ± 0.2 |
| Purified Water | q.s. 100% |

The results of a sedimentation/settling study comparing the physical stability of the Rimexolone steroid suspension of Example 8 to the commercially available prednisolone acetate steroid suspension (1 wt. %), Econopred®, are shown in FIG. 1. The Econopred® suspension contains hydroxypropyl methylcellulose as its polymeric viscosity enhancer. As indicated above, Example 8 contains Carbopol® as its stearic stabilizer and viscosity enhancer. After standing for six months in a measuring glass cylinder, 2% of the Econopred® suspension settled to the bottom as a cake or sediment. The remaining 98% consisted of a single supernatant phase. In contrast, none of the suspension of Example 8 settled to the bottom as a cake or sediment after standing for six months. Substantially all of the suspension of Example 8 remained flocculated (98%), topped with approximately a 2% supernatant layer. The suspension composition of Example 8 will return to its fully redispersed state after less than 5 seconds of gentle shaking by hand.

We claim:

1. A topical ophthalmic vehicle comprising: a negatively charged, water soluble polymer selected from the group consisting of carboxy vinyl polymers, sodium carboxy methylcellulose, pectin, gelatin (Type B), sodium hyaluronate, acacia, calcium carboxy methylcellulose, sodium alginate and polystyrene sulfonic acid; and a positively charged electrolyte selected from the group consisting of $Na^+$, $K^+$, $Mn^{++}$, $Ca^{++}$, $Mg^{++}$, $Fe^{++}$, $Fe^{+++}$, $Al^{+++}$, $Li^+$, $Zn^{++}$, $Be^{++}$, lysine○HCl, arginine○HCl and histadine○HCl; and wherein the concentrations of the polymer and the electrolyte are such that the vehicle is administrable as a drop and increases in viscosity upon instillation in the eye as a result of the migration of the positively charged electrolyte out of the vehicle.

2. The vehicle of claim 1 wherein the polymer concentration is from about 0.1 to about 10 wt. %.

3. The vehicle of claim 2 wherein the polymer concentration is from about 0.1 to about 3 wt %.

4. The vehicle of claim 1 wherein the electrolyte concentration is from about 0.01 to about 1 wt %.

5. The vehicle of claim 1 wherein the polymer is a carboxy vinyl polymer.

6. The vehicle of claim 5 wherein the polymer is Carbopol® carboxy vinyl polymer.

7. The vehicle of claim 1 wherein the electrolyte is selected from the group consisting of $Na^+$, $Ca^{++}$, and $Al^{+++}$.

8. The vehicle of claim 1 wherein the increase in viscosity upon instillation transforms the vehicle into a gel.

9. A pharmaceutical suspension composition which remains at least about 95% flocculated after standing for six months which comprises: a pharmaceutically active, water-insoluble drug and a suspension vehicle, wherein the suspension vehicle comprises a negatively charged, water soluble polymer selected from the group consisting of carboxy vinyl polymers, sodium carboxy methylcellulose, pectin, gelatin (Type B), sodium hyaluronate, acacia, calcium carboxy methylcellulose, sodium alginate and polystyrene sulfonic acid; and a positively charged electrolyte selected from the group consisting of $Na^+$, $K^+$, $Mn^{++}$, $Ca^{++}$, $Mg^{++}$, $Fe^{++}$, $Fe^{+++}$, $Al^{+++}$, $Li^+$, $Zn^{++}$, $Be^{++}$, lysine○HCl, arginine○HCl and histadine○HCl; and wherein the concentrations of the polymer and the electrolyte are such that the vehicle is administrable as a drop and increases in viscosity upon instillation in the eye as a result of the migration of the positively charged electrolyte out of the vehicle.

10. The suspension composition of claim 9 wherein the polymer is Carbopol® and the electrolyte is selected from the group consisting of $Na^+$, $Ca^{++}$, and $Al^{+++}$, and wherein the amount of Carbopol® is from about 0.1 to about 3 wt % and the amount of electrolyte is from about 0.01 to about 1 wt %.

11. A topical ophthalmic vehicle administrable as a drop which increases in viscosity upon instillation in the eye comprising:

a water soluble Carbopol® carboxy vinyl polymer and an electrolyte selected from the group consisting of $Na^+$, $Ca^{++}$, and $Al^{+++}$, wherein the amount of Carbopol® is from about 0.1 to about 3 wt % and the amount of electrolyte is from about 0.01 to about 1 wt %.

12. A topical ophthalmic vehicle administrable as a drop which increases in viscosity upon instillation in the eye comprising:

a positively charged, water soluble polymer selected from the group consisting of gelatin (Type A) and polyvinyl amine; and a negatively charged electrolyte selected from the group consisting of $PO_4^{-3}$, $HPO_4^{-2}$, $H_2PO_4^-$, $I^-$, $Cl^-$, $F^-$, $SO_4^{-2}$, $HCO_3$.

13. The vehicle of claim 12 wherein the polymer concentration is from about 0.1 to about 10 wt. %.

14. The vehicle of claim 13 wherein the polymer concentration is from about 0.1 to about 3 wt %.

15. The vehicle of claim 12 wherein the electrolyte concentration is from about 0.01 to about 1 wt %.

16. The vehicle of claim 12 wherein the increase in viscosity upon instillation transforms the vehicle into a gel.

17. A method delivering a drug to the eye which comprises:

topically administering a composition comprising a charged, water soluble polymer and an oppositely charged electrolyte at concentrations such that the composition is administrable as a drop and gels upon instillation as a result of the migration of the electrolyte out of the composition.

18. The method of claim 17 wherein the polymer is carboxy vinyl polymer and the electrolyte is selected from the group consisting of $Na^+$, $CA^{++}$, and $Al^{+++}$.

19. The method of claim 18 wherein the polymer is Carbopol® carboxy vinyl polymer.

* * * * *